United States Patent [19]

Pyne, Jr. et al.

[11] Patent Number: 4,882,274

[45] Date of Patent: Nov. 21, 1989

[54] METHOD FOR SOLUBILIZATION OF LOW-RANK COAL USING A CELL-FREE ENZYMATIC SYSTEM

[75] Inventors: John Pyne, Jr., Kennewick; Dorothy L. Stewart, Richland; James K. Fredrickson, Kennewick, all of Wash.; Martin S. Cohen, West Hartford, Conn.

[73] Assignee: Electric Power Research Institute, Inc., Palo Alto, Calif.

[21] Appl. No.: 69,709

[22] Filed: Jul. 6, 1987

[51] Int. Cl.$^4$ .......................... C12P 21/00; C12N 9/00
[52] U.S. Cl. ...................................... 435/68; 435/171; 435/183; 435/189; 435/190; 435/192; 435/264; 435/282; 435/262

[58] Field of Search ............... 435/264, 282, 183, 189, 435/190, 192, 68

[56] References Cited

PUBLICATIONS

Cohen et al., Chem. Abst., vol. 97 (1982), p. 75330U.

Primary Examiner—Sam Rosen
Attorney, Agent, or Firm—Flehr, Hohbach, Test, Albritton & Herbert

[57] ABSTRACT

A method is provided for isolating an extracellular product from white rot fungi. The extracellular product is useful for biosolubilizing low-rank coals to form water-soluble products.

7 Claims, 2 Drawing Sheets

METHOD FOR SOLUBILIZATION OF LOW-RANK COAL USING A CELL-FREE ENZYMATIC SYSTEM

The present invention is directed to a method for solubilizing low-rank coals with a cell-free enzymatic system which results in a water-soluble product useful as a fuel or fuel additive. The present invention also provides a method for producing the cell-free enzymatic system for this purpose.

BACKGROUND OF THE INVENTION

In nature, white-rot fungi, known lignin degraders, use plant matter as a source of nutrients, whereas the majority of microorganisms that live on plant matter do not degrade lignin. It is believed that lignin is a precursor of low-rank coals. A number of white-rot fungi are able to degrade low-rank coals as reported in the literature. See Cohen, et al., *Applied Environmental Microbiology*, 44: 23–27 (1982); Wilson, et al., *Proceedings of the Tenth Annual EPRI Contractors Conference on Coal Liquefaction*, May 6, 1986, Palo Alto, Calif.; Scott, et al., *Biotechnology Progress*, 2, 131–139 (1986); and Cohen, et al., *Proceedings of the Direct Liquefaction Contractors Meeting*, U.S. Department of Energy: Washington, D.C.; pages IV-48 to IV-64 (1986). The process of solubilizing low-rank coal with white-rot fungi has been termed "biosolubilization", indicating the metabolic origin of the soluble product. Work on biomineralization using German hard coals has been reported by Fakausa, Ph.D. thesis, Fredrich-Wilhelms University, Bonn, Federal Republic of Germany (1981); and the literature of bioconversion of coals, its relation to lignin degradation and work of lignin has been reviewed by Pyne and Wilson; *Biological Coal Beneficiation Literature Review*, Battelle Pacific Northwest Laboratory Report to the Electric Power Research Institute, May 1986.

However, the use of white rot broth cultures with the low-rank coal is not readily and economically adapted for production of useful products. Therefore it would be desirable to develop a method for the biosolubilization of low-rank coals in a cell-free environment which would be readily adaptable for use in industrial microbiological reactors or other readily available equipment.

It is therefore an object of the present invention to provide a method for producing a cell-free extract of white rot fungi comprising one or more enzymes which are capable of biosolubilizing low-rank coals.

It is a further object of the present invention to provide a method for biosolubilizing low-rank coals to a soluble product using a cell-free extract.

These and other objects of the present invention will be readily apparent from the following description, appended claims and by practice of the invention described herein.

SUMMARY OF THE INVENTION

The present invention provides a method for isolating an extracellular product derived from a culture of white rot fungi comprising the steps of fermenting the culture in a nutrient medium for a period of time sufficient to form extracellular fluid; separating the cells from the fermentation medium; filtering the resulting cell-free medium having a molecular weight cutoff of at least 10,000 MW; subjecting the retentate having a molecular weight of greater than or equal to 10,000 to chromatographic separation to isolate the fraction characterized by low-rank coal-degrading activity. The active fraction is then utilized to degrade low-rank coal into a water-soluble material.

DESCRIPTION OF THE PREFERRED EMBODIMENTS

Figure 1:
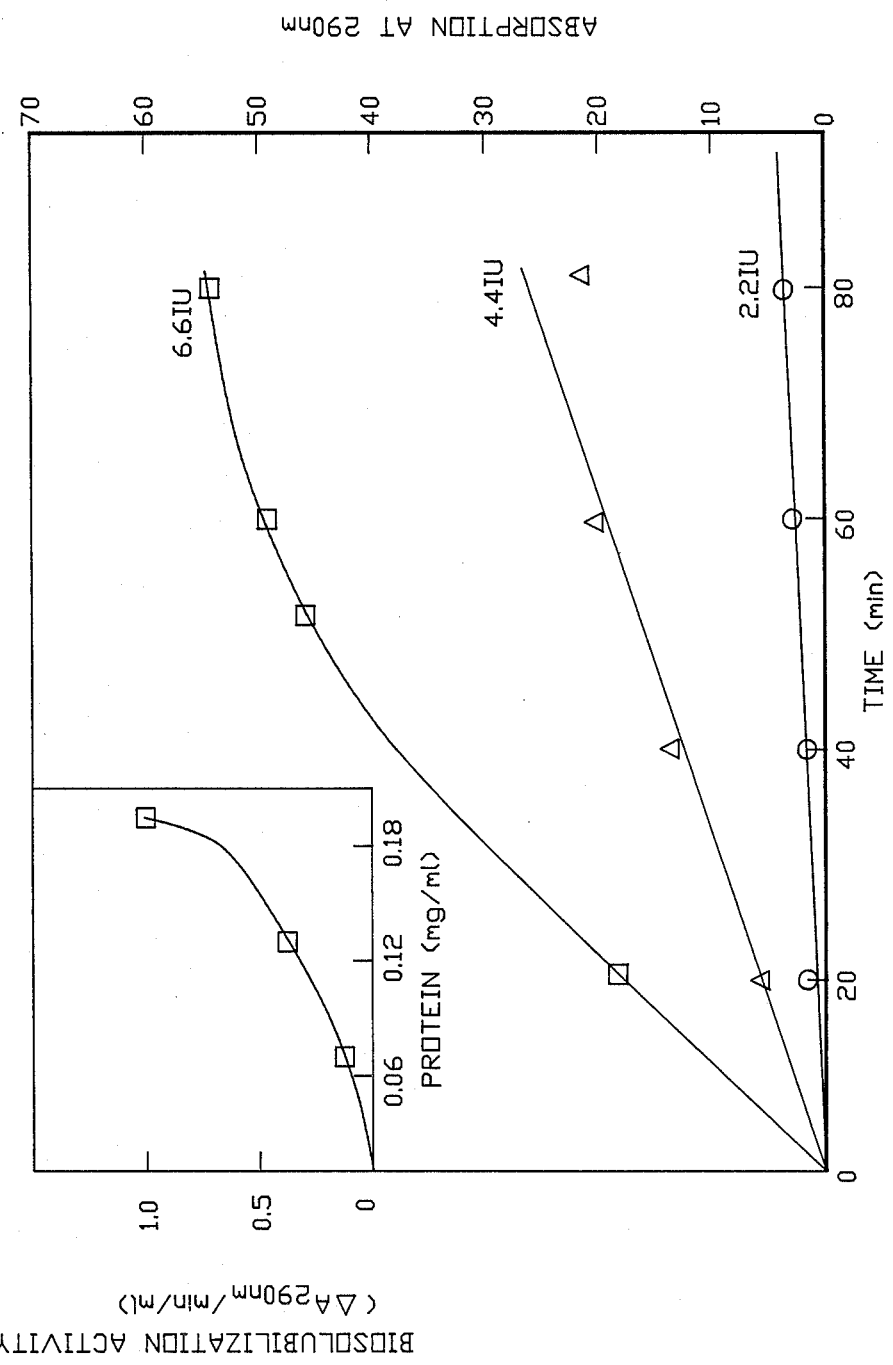
FIG. 1 is a graph of incubation time of a cell-free extract from *P. versicolor* with leonardite under conditions described in Example 1.

The present invention is applicable to a process for treatment of low-rank coals and coal processing byproducts, meaning those types of soft coals having high lignite content. Examples of such coals include leonardite and those coals generally characterized as lignites. The microorganism cultures from which the extracellular product with which the present invention is practiced derived from white-rot fungi including, but not limited to, *Polyporus versicolor, Phanerochaete, Penicillium Waksmanii, Aspergillus* and *Candida Sp. ML* 13. Not intending to be limited to a particular theory, in order to better understand the invention, it is believed that the extracellular product utilized in accordance with the present invention contains one or more enzymes which degrade lignin, the precursor from which low-rank coals are believed to be derived. Such enzymes may be lignase (also called lignin peroxidase), which catalyzes cleavage of aliphatic chains connecting aromatic rings at a carbon atom adjacent to the ring; laccase (a polyphenol oxidase), and/or cellobiose quinone oxidoreductase (CBQ), which reduces quinones to diphenols utilized by cells for growth and glucose oxidase which also assists in reducing quinones to diphenols.

The coals utilized in accordance with the present invention may be untreated, but are preferably pretreated by any one of the following methods in order to improve the microbial degradation. The low-rank coals may be pretreated with nitric acid and hydrogen peroxide in accordance with procedures disclosed by Scott, et al., *Biotechnology Progress* 2: 131–139 (1986). A particularly preferred pretreatment process is to expose the coal at temperatures above about 100° C. (most preferably at about 120° C.) for approximately five days.

Prior to treatment with the extracellular liquid having biosolubilization activity, the coal may be washed and sized, if desired, to improve its adaptability to the particular bioreactor apparatus utilized. This sizing procedure will be readily determinable by those of ordinary skill in the art.

Although many of the white rot fungi may be utilized, particularly those mentioned above, the most preferred is *Polyporus versicolor* and any strain thereof may generally be utilized. A stock culture may be routinely maintained, for example, in 5% Sabouraud maltose broth (30° C., 84–98% RH, pH 5.6). When needed, the culture may be grown to increase levels of the extracellular enzymes which have biosolubilization activity. Conditions for growing *Polyporus versicolor* are known in the art, for example, a growth medium may be used such as that described by Fahraeus, et al. *Acta Chemica Scandinavica* 21: 2367–2378 (1967). The fermentation may be initiated with an inoculum of *Polyporus versicolor* grown on Sabouraud maltose broth for seven to ten days at 25° with no agitation. The fungi grown under these conditions form a mycelial mat. The mats may be transferred to a vessel containing distilled water and a stirring apparatus (such as glass beads) and shaken vigorously, then the mycelial fragments may be transferred to the fermentor. To enhance the levels of the requisite extracellular enzymes (believed to have laccase-like activity), 2,5-xylidine may be added to the fermentor after about three days growth to increase extracellular enzyme production according to the procedure set forth by Fahraeus, et al., supra.

After a sufficient period of growth, the cell mass may be separated from the extracellular fluid by filtration. The resultant fluid may be filtered then through an ultrafilter, preferably with the molecular weight cut off of at least 100,000. The filtrate may then be concentrated further by again filtering through an ultrafilter having a molecular weight cutoff of at least 10,000. The resulting retentate may be washed (such as through a diafilter). By concentration a precipitate is formed which may be removed by filtration or centrifugation.

The thus obtained concentrated extracellular fluid is then chromatographed and the fraction having coal solubilizing activity is eluted and collected.

If the extracellular fluid is derived from *Polyporus versicolor*, the fraction containing the coal solubilizing activity coelutes with laccase activity, which may be measured using syringaldazine as a substrate (Bolag, et al., *Applied and Environmental Microbiology* 48: 849–854 (1984)). However, laccase activity is not the only indicator of coalsolubilizing activity, since commercially prepared laccase from *Aspergillus oryzae* (Sigma Chemical Co.) does not solubilize coal in vitro.

While the above descriptions are the preferred embodiments, other modifications may be made which are readily determinable by those of ordinary skill in the art and which are deemed to be within the scope of the present invention. For example, *Polyporus versicolor* will grow, in addition to the growth media described above, on glucose or succinate, as well as maltose as carbon sources. The lignite coal may also be sterilized prior to fermentation by using irradiation and/or autoclaving to decrease the risk of contamination of the cell culture.

The cell-free solubilizing-active preparation may be mixed with untreated low-rank coal (or with low rank coal prepared in any one of the methods described above, such as treatment for sterilization, granulation, oxidation, autoclaving, etc.) The cell-free preparation and the low-rank coal will be incubated together until the coal is solubilized. The respective amounts of cell-free preparation and coal will be readily determinable by those of ordinary skill in the art and will include consideration of such factors as the solubilizing activity of the particular preparation utilized, the type and method of preparation of the coal, the size of the run, configuration of apparatus utilized to contact the coal with the cell-free preparation, and the like.

The duration of incubation of the cell-free preparation with the coal will vary. Usually solubilization will be evident after about 24 hours of contact and, depending on the size and particular conditions of the incubation, complete solubilization may be obtained by incubation up to approximately 2 weeks.

Although not necessary, for convenience, the resulting biodegraded product may be precipitated with acid (usually by bringing the biodegraded mixture to about pH 2 with a mineral acid such as hydrochloric acid). A typical acid-precipitated, digested-coal product (from a cell-free extract of *Polyporus versicolor*) has somewhat controllable solubility characteristics due to the exchange of counterions by the acid precipitation. A soap-like product may be obtained by increasing, for example, the sodium counterion concentration, thereby rendering the product useful as an energy-rich surfactant to enhance the quality of coal/water slurries. Also, ion exchange may remove unwanted trace metals and provide more desirable counterions.

In one preferred embodiment of the biosolubilization reaction, the addition of citrate significantly enhances the biosolubilization reaction rate. While not determined to be critical, a preferred concentration of citrate in the biosolubilization reaction mixture comprising the cell-free extract and the coal is a citrate concentration of about 0.2 mM.

Uses of the biosolubilized coal product include its use as a polar liquid-soluble additive for blending with fuels as an extender. For example, the biosolubilized product may be blended with short chain alcohols to make a diesel fuel substitute. The process of solubilizing coals may be utilized for mining of thin-seam or marginal coal reserves which are presently uneconomical to mine and transport. These marginal coal reserves may be biosolubilized in situ (in the ground or in shallow pits) and then recovered by pumping the liquified material to the surface.

The biosolubilized material may also be utilized as a feedstock for acid-catalyzed methylation to produce high-quality fuels.

The biosolubilized product may also be used as a source for value-added chemicals, such as surfactants or bioactive compounds, whereby these chemicals would be separated from the raw biosolubilized product and the residue used as a fuel.

Having described the invention and the preferred embodiments thereof, the following examples are provided by way of illustration. However, the following examples are not intended to nor should they be construed as imposing a limitation on the invention.

EXAMPLE 1

An extracellular product was obtained from *Polyporus versicolor* as follows. The inoculum used for he fermentation was three 50 ml culture of *Polyporus versicolor* grown on Sabouraud-maltose broth (Cohen, et al., *Appl. Environ. Microbiol.*, 44, 23–27 (1982)) for 7 to 10 days at 25° C. with no agitation. The fungi grown under these conditions forms a mycelial mat. The mats were transferred to a stopped vessel containing 250 mls distilled water and 50 mls of 3 mm glass beads. This vessel was shaken vigorously and the mycelial fragments were transferred to the fermentor. The fungus was grown in a Chemap CF-20 fermentor at 25° C., and was supplied with 4 L. of filtered air per minute at atmospheric pressure to 15 L. of the growth medium published by Fahraeus, et al. (*Acta Chem. Scan.* 21, 2367–78 (1967)). A two-stage Rushton turbine (6-blade) agitator system was used at a speed of 400 R.P.M. After three days growth in the fermentor, 0.3 ml of 2,5-xylidine (Aldrich Chemical, Milwaukee, WI) was added to increase levels of extracellular polyphenol oxidase. The extracellular fluid formed during the growth was separated from cell mass by filtration through several layers of cheesecloth. The resultant fluid was then filtered through an ultrafiltration membrane with a molecular weight cutoff of 100,000 (Amicon H5P 100–43). The high molecular weight material in the aqueous fluid was concentrated using an ultrafiltration membrane with a molecular weight cutoff of 10,000 (Amicon H5P 10–43). The resulting fluid (1 L.) was further washed (diafiltered) with three 300 ml portions of water while being continually passed through the H5P 10–43 membrane to maintain a constant volume of 1 L. The concentration and diafiltration steps caused precipitate formation which was removed by either filtration or centrifugation. The concentrated extracellular fluid was then chromatographed on a 2 cm×30 cm DEAE-cellulose (Amicon cellufine DEAE-AM). The column had previously been equilibrated to 0.01 M sodium phosphate, pH 7.0 buffer. The coal solubilizing activity was eluted from the column with a linear salt gradient of 0 to 0.5 M sodium chloride. The coal solubilizing activity coeluted with a polyphenol oxidase activity. The polyphenol oxidase activity was measured using syringaldazine as a substrate (Bollag and Leonowicz, 1964). Several types of coal were tested for in vitro solubilization by the cell-free fluid.

The in vitro assay for biological conversion of coal consisted of incubating ground coal (150–200 micrometers) with fractions from the DEAE-cellulose column. Although several coals could be solubilized in vitro, the coal used in routine assays was leonardite obtained from American Colloid Co. (Skokie, IL). The total volume of the assay mixture was 1 ml and contained 100 micromoles sodium phosphate at pH 5.2 and 10mg of leonardite. The assay mixture was typically incubated for 20 minutes at 23° C. (room temperature) with occasional manual agitation. After incubation the mixture was briefly centrifuged in a desktop clinical centrifuge for 30 seconds to separate the coal from the liquid. An aliquot of the supernatant was removed, diluted in water and its absorbence at 290 nm measured with a spectrophotometer. FIG. 1 shows the time course of the solubilization reaction using different amounts of extracellular fluid containing the polyphenol oxidase enzyme.

Figure 2:
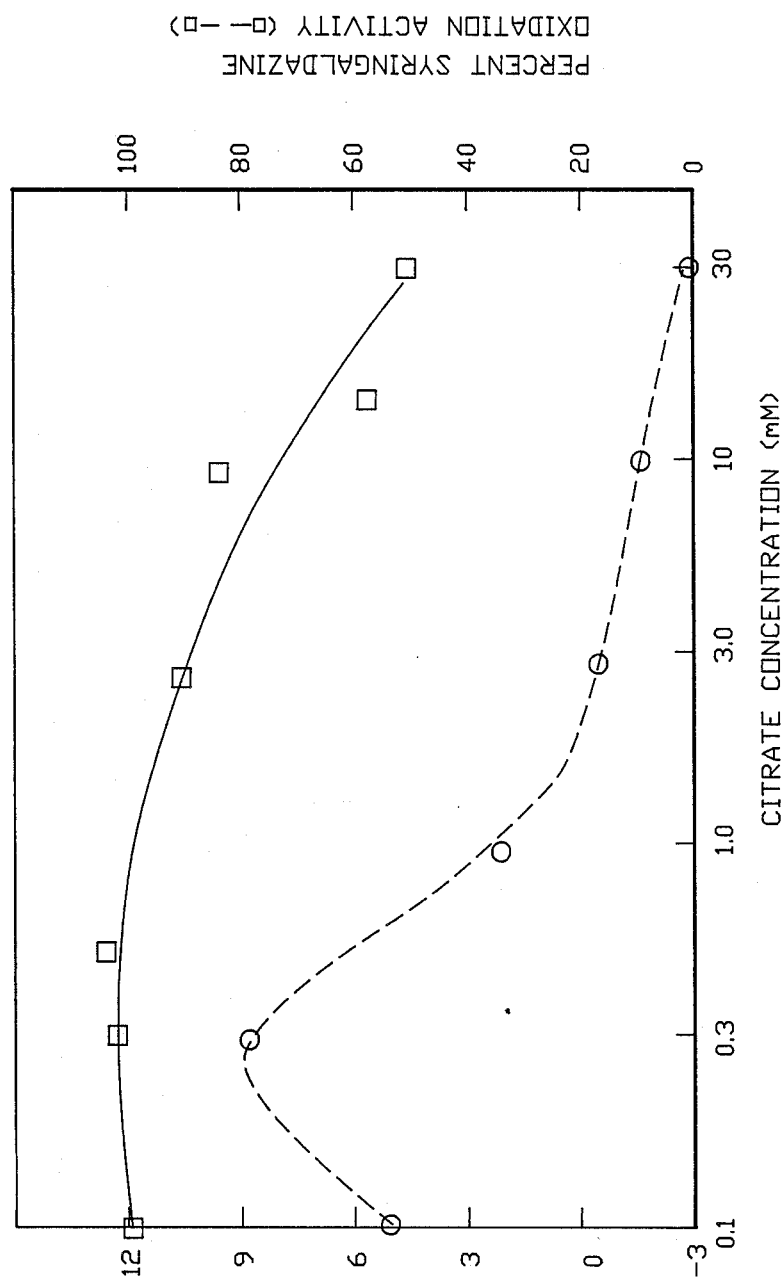
FIG. 2 is a graph of various citrate concentrations used in enzymatic solubilization of leonardite observed under conditions described in Example 1.

While investigating the in vitro solubilization reaction, citrate was found to significantly enhance the reaction rate (FIG. 2). The optimal concentration of citrate was 0.2 mM. The combination of a coal oxidative pretreatment by exposure to air at above 100° C. for 5 days, a concentrated *Polyporus versicolor* extracellular enzyme preparation and inclusion of 0.2 mM citrate in the reaction mix make in vitro solubilization of low-rank coals readily measurable.

EXAMPLE 2

A *Polyporus versicolor* sample was obtained from the American Type Culture Collection (ATCC 12679), and cultures were routinely maintained in 5% Sabouraud-maltose broth (30° C., 84–98% RH, pH=5.6). All fungal transfers were done aseptically in a flow hood. All materials that came in contact with the fungi were sterilized prior to use. Leonardite coal particles were washed for 10 minutes with mixing. The resulting liquid was removed by vacuum filtration through Whatman #42 filter paper and discarded. The remaining coal was dried and sized to less than 500 microns by sieving. Coal particles less than 500 microns were further sized by sieving. Three sieves were used to obtain 3 sized groups of 250–150, 149–105, and less than 105 microns. The 250–500 micrometer coal was discarded.

Twelve cultures were inoculated with 1 mL of a hyphal suspension of *Polyporus* per 25 mL of broth and were grown for 14 days in stationary culture. Continuous mycelial mats were formed and pieces of sterile coal were added on top of the mycelium. The media from one culture was harvested each day by vacuum filtration. This procedure was initiated on the day following the addition of coal to the mycelial mats, day 1, and was terminated on day 8. The filtrates were frozen at the time of harvest and were stored that way until the contents were analyzed. The filtrates were thawed, their liquification rates were determined by spectroscopy and protein concentration of each was determined using the Biuret method. The pH value was recorded at the start and finish of each rate determination.

Additional tests were done in the same way except that the cultures were harvested over a 12-day period which was designated day −2 through day 9. Day 0 corresponds to day 14 after inoculation of the sterile broth with the hyphal suspension. The liquification rates of these filtrates were determined fresh and after being frozen one time. The pH was adjusted to pH =5.5 for the start of the rate determinations and the pH at the end of the measurements was recorded.

To test for the effect of pH on liquefication, pH values of the buffers in 8 tubes containing 3 mL of buffer each were adjusted using 1.0 M HCl or 1.0 M NaOH. A range of pH=4.0 to pH=7.5 in 0.5 pH unit increments was made. To each of these tubes, 30 mg of washed coal was added and the absorbance at 450 nm was determined for each sample over a 4 hour period.

To test for the effect of coal particle size on liquefaction, leonardite coal of three defined group sizes was compared as substrates in the liquefaction assay. The groups were 250–150 um, 149–105 um, and less than 105 um sizes. Samples from each group of coal size were subjected to liquefaction using pooled day 8 filtrates and appropriate blanks. The resulting absorbance at 450 nm was determined over a 3-hour period. Each group was analyzed in triplicate and the procedure was repeated once. Freshly prepared, sterile broth was substituted for the filtrate in the blanks.

Table 1 shows the change in absorbance of solutions which contain phosphate buffer over a range from pH =4.0 to pH=7.5. The results indicate that, below pH=5.5, the changes in absorbance are small and approximately the same indicating that little coal has been solubilized. The change in absorbance at pH =6.0 is slightly higher than that of the pH 5.5 group and significantly less than that of the ph=6.5 and higher group.

Table 2 shows the results of rates of liquefaction on three defined coal particle size groups. The study was done twice using filtrates from day 8 cultures and freshly prepared Saboraud-maltose broth (SMB) as a control. The two groups containing 250 to 149 um and 149–105 um particle sizes give lower rates of reaction then does the 105 um particle size group. The reactions containing SMB give background liquefication rates which are similar for all three particle size groups.

TABLE 1

| EFFECT of pH on COAL SOLUBILIZATION | | | | |
|---|---|---|---|---|
| Ph | 1.0 hrs. | 2.0 | 3.0 | 4.0 |
| 4.0 | 0.078 | 0.100 | 0.109 | 0.126 |
| 4.5 | 0.081 | 0.119 | 0.145 | 0.158 |
| 5.0 | 0.094 | 0.150 | 0.158 | 0.182 |
| 5.5 | 0.105 | 0.168 | 0.211 | 0.222 |
| 6.0 | 0.228 | 0.332 | 0.440 | 0.519 |
| 6.5 | 1.643 | 2.707 | 3.408 | 3.804 |
| 7.0 | 3.812 | 3.779 | 3.771 | 3.771 |

TABLE 1-continued

| \multicolumn{5}{c}{EFFECT of pH on COAL SOLUBILIZATION} |
| Ph | 1.0 hrs. | 2.0 | 3.0 | 4.0 |
| --- | --- | --- | --- | --- |
| 7.5 | 3.815 | 3.745 | 3.650 | 3.650 |

TABLE 2

EFFECT OF PARTICLE SIZE ON LIQUIFICATION

| | Hrs. | | | | | |
| --- | --- | --- | --- | --- | --- | --- |
| Contents of Tube | 0.5 | 1.0 | 1.5 | 2.0 | 2.5 | 3.0 |
| Filtrate + 250–149 um | 0.137 | 0.251 | 0.363 | 0.509 | 0.685 | 0.881 |
| Filtrate + 149–105 um | 0.113 | 0.239 | 0.378 | 0.522 | 0.711 | 0.919 |
| Filtrate + less than 105 um | 0.511 | 0.683 | 0.867 | 1.083 | 1.287 | 1.502 |
| SMB + 250–149 um | 0.027 | 0.073 | 0.096 | 0.101 | 0.175 | 0.133 |
| SMB + 149–105 um | 0.039 | 0.077 | 0.088 | 0.085 | 0.098 | 0.097 |
| SMB + less than 105 um | 0.059 | 0.094 | 0.092 | 0.100 | 0.116 | 0.128 |

EXAMPLE 3

Four sources of lignite substrate were assessed for bioconversion by *Polyporus versicolor* cultured on Sabouraud-maltose agar for six days before addition of the autoclaved lignites. Of the four lignites examined, only with the North Dakota Leonardite obtained from American Colloid was there evidence of degradation after three weeks incubation. Leonardite showed evidence of coal solubilization within 24 hours after the lignite was added to the cultures. The three coals showing no degradation (Texas lignite, North Dakota Beulah #3 and the North Dakota Beulah Zap) were stored under nitrogen prior to autoclaving and addition to Polyporus cultures, allowing little opportunity for oxidation.

Illinois #6 (bituminous) coal was treated with 17% perchloric acid and stirred for 48 hours. After 7 days incubation with Polyporus, some conversion was apparent. Similar results were obtained after 2 months' incubation with Aspergillus.

EXAMPLE 4

Stock cultures of *Polyporus versicolor* are routinely maintained in both solid Sabouraud-maltose agar and Sabouraud-maltose broth cultures. All cultures wre incubated at 30° C.; relative humidity, 84 to 98%; and pH, 5.8. Experimental cultures were also incubated as described above, with the exception of the experiments involving specific additions to the media. Solid cultures were inoculated with a hyphal suspension and allowed to incubate for approximately 12 days to produce a continuous fungal mat. Sterile lignite pieces (approximately 5 mm$^3$) were placed directly on the hyphal mat. Although extensive solubilization was evident after 24 hours, product was harvested from the cultures after 5 days and freeze-dried, using a Bellco cold finger at 70° C., and stored in a desiccator at room temperature. All data reported here were obtained on the freeze-dried bioextract.

Coal Solubilization. Samples of leonardite coal digested to a black, viscous liquid. Solubilization was visually apparent within 24 hours after the leonardite was added to the cultures. The amount of black liquid product continuously increased until the lignite was completely liquefied or the growth of the fungi ceased, possibly from the effects of toxic products produced during the process of solubilization. The bioextract appeared to contain no particulate matter when observed at a magnification of 400X, using a compound microscope.

Solubility Tests. When the bioextract was mixed with solvents having polarity indices less than 4, such as hexane (0), methylene chloride (3.4), and 1-butanol (3.9), the solvents appeared to have little, if any effect on the freeze-dried solid (FIG. 1). Mixing the bioextract with solvents that had polarity indices between 4 and 6.2, such as tetrahydrofuran (4.2), 1-propanol (4.3), and ethanol (5.2), resulted in formation of a light-colored, yellowish-brown solution. This indicated increasing solubility of the bioextract compared with that obtained with the solvents of lower polarity mentioned above. The bioextract was most soluble in water, resulting in an opaque, black solution. Solubility of the starting leonardite was less than 1 mg/ml for all six solvent tested, even after a 6-day period of solvent exposure.

Titration. Two titrations were performed. For one, 0.3254 g of the acid-precipitated material was placed in a beaker with 20.00 mL of water. A total of 1.2500 mL of base was added (5.0-mL increments) at 6-second intervals. The 6-second period was the minimum needed to insure homogeneity after each addition of titrant. For the second titration, we used 0.01225 g of the acid-precipitated material in 20.00 mL of water. In this case, 2.1500 mL of titrant was added (10.0-mL increments) at 20-minute intervals.

There were no distinct endpoints in the titrations, indicating the presence of weak acids having a wide range of acid constants. In the early stages of the titration, some of the buffering capacity was due to the base-assisted dissolution of the solid. Once the solution became basic, there was evidence for a slow reaction of hydroxide ion with the coal ions in solution. The plot of the slower titration indicates that the hydroxide ion continued to react slowly with the sample. After slow addition of more than 20 mmoles OH$^-$, sample pH remained at 11. The kinetic effect can be seen in the comparison of the two titrations. The data at 5 minutes per point have more free hydroxide (a higher pH) earlier in the titration, with an even more pronounced effect when the base was introduced as fast as possible.

The titration curves indicate that approximately 4 to 5 moles of base were needed to neutralize 1000 g of the coal sample, an amount corresponding to an equivalent weight of 200 to 250 g/equivalent.

Calorimetry. The average energy content of the freeze-dried leonardite coal sample was 4.394 Kcal/g (7,378 Btu/lb). Average energy content for the bioextract was 4.208 Kcal/g, equivalent to 95.7% of the original energy content of the lignite on a gram-for-gram basis (1 g of feed coal yielded less than 1 g of solid bioextract in solution). The maximum error of these measurements was 1.2%, determined by measuring the energy content of naphthalene.

Estimation of Molecular Weight and Molecular-Weight Distribution

The molecular weight of the bioextract, as estimated by vapor-pressure osmometry, was 342+18 daltons. This apparently low value is likely due to the contribution of low-molecular weight counterions, such as sodium, potassium, and ammonium. Adjustment of pH altered the apparent molecular weight of the material, as determined by ultrafiltration. This shift to lower apparent molecular weight at higher pH is consistent with the NMR data, which showed a high concentration of carboxylic acid groups, and suggests that the apparent molecular weight of the material is altered by hydrogen bonding at lower pH.

It is claimed that:

1. A method of isolating an extracellular product derived from a culture of white rot fungi comprising the steps of fermenting the culture of said fungi in a nutrient medium for a period of time sufficient to form extracellular fluid, separating the cells from said medium and filtering the resulting cell-free medium through a filtration means having a molecular weight cutoff of at least 10,000 molecular weight; subjecting the retentate of molecular weight greater than 10,000 to chromatographic separation to isolate a low-rank coal-degrading active fraction.

2. A method of degrading solid low-ranked coal to a water-soluble material by enzymatic action comprising the step of contacting said low-ranked coal with a cell-free extracellular material derived from fermentation of white rot fungi characterized by low-rank coal-degrading activity.

3. A solubilized coal product produced according to the process of claim 2.

4. A method according to claim 1 wherein said fungi comprises *Polyporus versicolor*.

5. A method according to claim 2 wherein said fungi comprises *Polyporus versicolor*.

6. A product according to claim 3 wherein said fungi comprises *Polyporus versicolor*.

7. A method according to claim 2 wherein said step is conducted in the presence of citrate.

* * * * *

UNITED STATES PATENT AND TRADEMARK OFFICE
CERTIFICATE OF CORRECTION

PATENT NO. : 4,882,274

DATED : November 21, 1989

INVENTOR(S) : Pyne, Jr. et al.

It is certified that error appears in the above-identified patent and that said Letters Patent is hereby corrected as shown below:

In Item 75 on the first page of the patent before "all of Wash.:" please add --Bary W. Wilson, Kennewick--

Signed and Sealed this

Second Day of July, 1991

Attest:

HARRY F. MANBECK, JR.

Attesting Officer

Commissioner of Patents and Trademarks